(12) United States Patent
Goeke

(10) Patent No.: US 7,691,802 B2
(45) Date of Patent: Apr. 6, 2010

(54) ALCOHOLS AND KETONES OF B1- AND TRICYCLIC COMPOUNDS AND ODORANT COMPOSITIONS

(75) Inventor: Andreas Goeke, Dübendorf (CH)

(73) Assignee: Givaudan SA, Vernier (CH)

( * ) Notice: Subject to any disclaimer, the term of this patent is extended or adjusted under 35 U.S.C. 154(b) by 1290 days.

(21) Appl. No.: 10/518,565

(22) PCT Filed: Jun. 20, 2003

(86) PCT No.: PCT/CH03/00401

§ 371 (c)(1),
(2), (4) Date: Dec. 20, 2004

(87) PCT Pub. No.: WO04/000776

PCT Pub. Date: Dec. 31, 2003

(65) Prior Publication Data

US 2005/0239683 A1    Oct. 27, 2005

(30) Foreign Application Priority Data

Jun. 21, 2002   (GB) ................................ 0214344.4

(51) Int. Cl.
*A61K 8/30* (2006.01)
*A61K 8/18* (2006.01)
*A61K 7/46* (2006.01)
*A61Q 13/00* (2006.01)
*C11D 9/00* (2006.01)
*C07C 35/00* (2006.01)
*C07C 35/37* (2006.01)
*C07C 49/00* (2006.01)
*C07C 49/443* (2006.01)
*C07C 49/453* (2006.01)
*C07C 49/633* (2006.01)
*C07C 49/643* (2006.01)

(52) U.S. Cl. .............................. 512/14; 512/15; 512/16; 512/17

(58) Field of Classification Search .................... 512/14, 512/15, 16, 17
See application file for complete search history.

(56) References Cited

U.S. PATENT DOCUMENTS

| | | | | |
|---|---|---|---|---|
| 3,679,750 A | * | 7/1972 | Mookherjee | 568/373 |
| 3,814,704 A | * | 6/1974 | Mookherjee | 424/69 |
| 4,011,269 A | | 3/1977 | Naf et al. | 260/617 |
| 4,947,002 A | | 8/1990 | Frater et al. | |
| 5,817,616 A | * | 10/1998 | Zhen et al. | 512/14 |
| 6,191,312 B1 | | 2/2001 | Hagemeyer et al. | |

OTHER PUBLICATIONS

STIC "Registry File" Structure Search of the compound of formula I, as set forth in applicant's independent claim 1. (Apr. 20, 2009), pp. 1-48 of search were printed and made of record.*

Search Report from the Patent Office in Great Britain dated Nov. 26, 2002 for Application No. GB 0214344.4.
Abstract only: CAPLUS Abstract Accession No. 2000:184161 & Tertrahedron vol. 56, No. 11, 2000, Hisahiro Hagiwara et al., "Bisannelation with vinyl selenoxide: synthesis of tricycle[3.2.1.0$^{2.7}$]octan-6-one and its congeners", pp. 1445-1449.
Abstract only: CAPLUS Abstract Accession No. 1995:818045 & Bulletin of the Chemical Society of Japan vol. 68, No. 9, 1995, Tadao Uyehara et al., "Rearrangement approaches to cyclic skeletons. IX. Stereoselective total synthesis of (±)-campherenone based on a ring-contraction of bicycle[3.2.1]oct-6-en-2-one. Reliable one-step diazo transfer followed by a Wolff arrangement", pp. 2687-2694.
Abstract only: CAPLUS Abstract Accession No. 1989:595125 & Kexue Tongbao (Foreign Language Edition) vol. 33, No. 18, 1988, John V Turner & Xinfu Pan, "Synthesis of optically active helminthosporic acid", pp. 1528-1529.
Abstract only: CAPLUS Abstract Accession No. 1986:148365 & Canadian Journal of Chemistry vol. 63, No. 10, 1985, Robert M Cory et al., "Nitrooelfin bicycloannulation: one-step sunthesis of tricycle[3.2.1.0$^{2.7}$]octan-6-ones from cyclohexenones and of tricycle [2.2.1.0$^{2.6}$]heptan-3-ones from cyclopentenones", pp. 2618-2627.
Abstract only: CAPLUS Abstract Accession No. 1984:610054 & Synthesis vol. 6, 1984, L R Subramanian et al., "Hydrogenative cleavage of phenolic and enolic perfluoroalkanesulfonates", pp. 481-485.
Abstract only: CAPLUS Abstract Accession No. 1982:34323 & Journal of Organic Chemistry vol. 47. No. 2, 1982, Semiramis Ayral-Kaloustian & William C Agosta, "Pyrolysis of the tosylhydrazone sodium salts of two bicyclic lactones", pp. 284-287.
Abstract only: CAPLUS Abstract Accession No. 1981:3780 & J. Chem. Soc., Perkin Trans. 1, vol. 7, 1980, Gopala Gowda & T Brian H McMurry, "Photochemistry of substituted cyclic enones. Part 2.5-[Prop-2-enyl]cyclopentenones", pp. 1516-1522.
Abstract only: CAPLUS Abstract Accession No. 1977:467743 & J. Am. Chem. Soc. vol. 99, No. 10, 1977, William C Agosta & Steven Wolff, "Photochemistry of bicycle[3.2.1]octan-6-ones. Stereoselectivity of hydrogen transfer in disproportionation of biradical intermediates", pp. 3355-3361.

(Continued)

*Primary Examiner*—Joseph D Anthony
(74) *Attorney, Agent, or Firm*—Norris McLaughlin & Marcus, PA

(57) ABSTRACT

Novel compounds of formula I and their use in flavour and fragrance compositions.

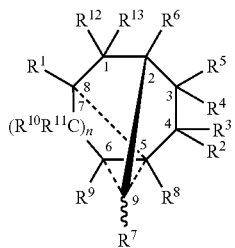

$R^1$ to $R^{13}$ have the meaning as described in the specification.

16 Claims, No Drawings

OTHER PUBLICATIONS

Abstract only: CAPLUS Abstract Accession No. 1976:522984 & J. Am. Chem. Soc. vol. 98,No. 14, 1976, William C Agosta & Steven Wolff, "The photochemistry of substituted bicycle[3.2.1]octan-6-ones. Chair-chair conformational inversion of biradical intermediates", pp. 4182-4188.

Abstract only: CAPLUS Abstract Accession No. 1975:585846 & J. Org. Chem. vol. 40, No. 11, 1975, William C Agosta & Steven Wolff, "220-MHz nuclear magnetic resonance spectra of bicycle [3.2.1]octan-6-ones from substituted cyclohexyl diazo ketones", pp. 1665-1668.

Abstract only: CAPLUS Abstract Accession No. 1975:496520 & J. Org. Chem. vol. 40, No. 8, 1975, William C Agosta & Steven Wolff, "Preparation of bicycle[3.2.1]octan-6-ones from substituted cyclohexyl diazo ketones", pp. 1027-1030.

International Search Report for application PCT/CH03/00401 dated Sep. 12, 2003.

International Preliminary Examination Report for application PCT/CH03/00401 dated Feb. 11, 2004.

Search Report from The Patent Office in the United Kingdom for application GB 0214344.4 dated Nov. 26, 2002.

Froestl, Wolfgang et al: "Intromolecular '2 + 2!-photocycloadditions of 6-allyl-2cyclohexenones. Formation of tricycle '3.3.1.02.7!nonan-6-ones and tricycle '44.2.1.03,8!nonan-7-ones", Helvetica Chimica Acta (1976), 59(6), 2244-8, XP002254317, p. 2246.

Cruciani, Giuliano et al: "Regiochemical trends in intramolecular '2 + 2! Photocycloadditions of 6-(prop-2-enyl)cyclohex-2-enones and 5-(prop-2-enyl)cyclopent-2-enones", Helvetica Chimica Acta (1990), 73(2), 288-97, XP002254318, p. 290.

Cory, Robert M. et al: "Vinyl phosphonium bicycloannulation of cyclohexenones and trachyloban-19-oic acid", Journal of Organic Chemistry (1980), 45(10), 1852-63, XP002254319, p. 1861, p. 1862.

* cited by examiner

ALCOHOLS AND KETONES OF B1- AND TRICYCLIC COMPOUNDS AND ODORANT COMPOSITIONS

This invention relates to novel compounds having woody, vetiver and patchouli-like odour notes. This invention relates furthermore to a method for their production and to flavour and fragrance compositions containing them.

Compounds having woody, vetiver and patchouli-like odour notes are described in the literature, for example the class of sesquiterpenes that naturally occur in essential oils and which can be isolated by water-steam distillation of a plant or parts of a plant. This process is very cost intensive and the quality and the odour as well as the flavour characteristics of the isolated compounds may vary with the climate and the origin of the plant. Thus, there is an ongoing demand in the fragrance and flavour industry for new compounds imparting, enhancing, or improving woody, vetiver and patchouli-like notes.

Tricyclic sesquiterpenes, in particular patchoulol and derivatives thereof have been disclosed in the U.S. Pat. No. 4,011,269. The compounds described therein develop odoriferous notes the character of which is reminiscent of that of patchouli oil.

We have now found a novel class of compounds having much sought after woody, vetiver and patchouli-like odour notes and which may be produced from synthetic starting materials.

In a first aspect the invention provides a compound of the formula I

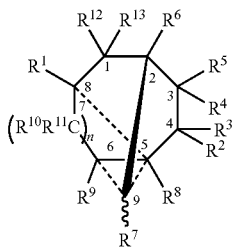

wherein $R^1$, $R^4$, $R^6$ and $R^7$ are independently hydrogen, methyl or ethyl;

$R^2$ and $R^3$ are independently hydrogen, or $C_{1-5}$ alkyl, e.g. methyl, ethyl, or linear or branched propyl, butyl, or pentyl; or $R^2$ and $R^3$ together with the carbon atom to which they are attached form a 5- or 6-membered cycloylkyl ring;

$R^5$ is hydrogen, or $C_{1-4}$ alkyl, e.g. methyl, ethyl or linear or branched propyl;

$R^8$ is hydrogen, or branched lower $C_{3-7}$ alkyl, e.g. isopropyl, tert. butyl;

$R^9$ is hydrogen, methyl, ethyl, or branched lower $C_{3-7}$ alkyl, e.g. isopropyl, tert. butyl;

$R^{10}$ is ethyl or propyl;

$R^{11}$ is $C_{1-4}$ alkyl, e.g. methyl, ethyl, or linear or branched propyl or butyl;

$R^{12}$ is hydroxy;

$R^{13}$ is hydrogen, or $C_{1-4}$ alkyl, e.g. methyl, ethyl, or linear or branched propyl or butyl; or $R^{12}$ and $R^{13}$ together with the carbon atom to which they are attached form a carbonyl group;

the dashed line represents either a C—C single bond or no bond; and a) when C5 and C8 are connected by single bond and C9 and C6 are connected by a single bond, C9 and C5 are not connected by a bond, n=1, $R^7$, $R^8$ are hydrogen, and $R^9$ is hydrogen, methyl or ethyl; or b) when C5 and C8 are connected by a single bond and C9 and C6 are connected by a single bond, C9 and C5 are not connected, n=0, $R^7$, $R^8$ is hydrogen, $R^9$ is a branched lower $C_{3-7}$ alkyl; or c) when C5 and C8 are not connected by a bond, C9 and C5 are connected by a single bond, $R^7$ is hydrogen, methyl or ethyl, $R^8$ is a branched lower $C_{3-7}$ alkyl, or $R^7$ and $R^8$ together with the carbon atoms to which they are attached form a 5- or 6-membered cycloalkyl ring, n=0, and the bond between C6 and C8 may be a single bond or a double bond.

Preferred compounds are those of the formulae Ia, Ib and Ic

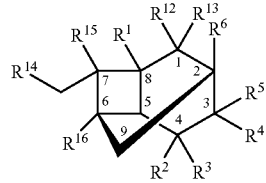

Ia

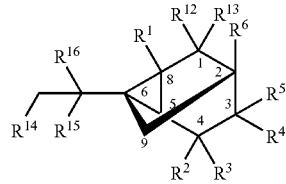

Ib

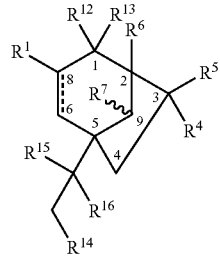

Ic wherein $R^1$, $R^4$, $R^6$, and $R^{16}$ are independently hydrogen, methyl or ethyl;

$R^7$ and $R^{14}$ are independently hydrogen, methyl or ethyl; or, $R^7$ and $R^{14}$ together with the carbon atoms to which they are attached form a 5- or 6-membered cycloalkyl ring;

$R^2$ and $R^3$ are independently hydrogen, or $C_{1-5}$ alkyl, e.g. methyl, ethyl, or linear or branched propyl, butyl, or pentyl; or, $R^2$ and $R^3$ together with the carbon atom to which they are attached form a 5- or 6-membered cycloalkyl ring;

$R^5$ is hydrogen, or $C_{1-4}$ alkyl, e.g. methyl, ethyl, or linear or branched propyl;

$R^{15}$ is $C_{1-4}$ alkyl, e.g. methyl, ethyl, or linear or branched propyl;
$R^{12}$ is hydroxy;
$R^{13}$ is hydrogen or $C_{1-4}$ alkyl, e.g. methyl, ethyl, or linear or branched propyl; or
$R^{12}$ and $R^{13}$ together with the carbon atom to which they are attached form a carbonyl group; and
in formula Ic the bond between C6 and C8 may be a single bond, or the dotted line together with the bond between C6 and C8 may represent a double bond.

The compounds according to the present invention contain one or more chiral centres and as such may exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methodology known in the art, e.g. preparative HPLC and GC or by stereoselective syntheses.

Particular preferred compounds of formula Ia are 1,5,7,8,8-Pentamethyl-tricyclo[3.3.1.0$^{2,7}$]nonan-6-one, 1,5,7,8,8-Pentamethyl-tricyclo[3.3.1.0$^{2,7}$]nonan-6-one, 1,3,3,5,7,8,8-Heptamethyl-tricyclo[3.3.1.0$^{2,7}$]nonan-6-one, 3,3,5,7,8,8-Hexamethyl-tricyclo[3.3.1.0$^{2,7}$]nonan-6-one, 3,3,5,8,8-Pentamethyl-tricyclo[3.3.1.0$^{2,7}$]nonan-6-one, 5,7,8,8-Tetramethyl-tricyclo[3.3.1.0$^{2,7}$]nonan-6-one, and 5,6,7,8,8-Pentamethyl-tricyclo[3.3.1.0$^{2,7}$]nonan-6-ol.

A particular preferred compound of formula Ib is 1-Isopropyl-3,3,5-trimethyl-tricyclo[3.2.1.0$^{2,7}$]octan-6-one.

Particular preferred compounds of formula Ic are 5-Isopropyl-1,3-dimethyl-bicyclo[3.2.1]oct-3-en-2-one, 5-Isopropyl-1,3-dimethyl-bicyclo[3.2.1]octan-2-one, 5-tert-Butyl-1,3-dimethyl-bicyclo[3.2.1]oct-3-en-2-one, 5-sec-Butyl-1,3-dimethyl-bicyclo[3.2.1]oct-3-ene-2-one, 5-Isopropyl-3-methyl-bicyclo[3.2.1]oct-3-ene-2-one, 5,7-Diisopropyl-3-methyl-bicyclo[3.2.1]oct-3-en-2-one, 5-Isopropyl-3,7,7-trimethyl-bicyclo[3.2.1]oct-3-en-2-one, and 1,3,5-Trimethyl-1,5,6,7,8,8a-hexahydro-1,4a-ethano-naphthalen-2-one.

In another aspect the invention provides flavour and fragrance compositions comprising a compound of formula I or mixtures thereof, more particularly compounds of formula Ia, Ib, or Ic or mixtures thereof. Particular preferred are compositions that comprise at least one compound of formula Ia and one compound of formula Ic.

In addition, the compounds may be used in combination with a basis material. As used herein, the "basis material" includes all known odourant molecules selected from the extensive range of natural and synthetic molecules currently available, such as essential oil, alcohols, aldehydes and ketones, ether and acetals, ester and lactones, macrocycles and heterocycles, and/or in admixture with one or more ingredients or excipients conventionally used in conjunction with odourants in fragrance compositions, for example carrier materials, and other auxiliary agents commonly used in the art.

In one embodiment, the compounds of the present invention may be used in fragrance applications, e.g. in any field of fine and functional perfumery.

In another embodiment, the compounds of the present invention may be used in flavour applications and are particularly useful in modifying for example strawberry and raspberry flavours but also brown flavours. They may be used in herbal mixtures and teas. The compounds of the present invention are also well suited for example in mouthwash applications.

In flavourant applications, the compounds of the present invention may be present in compositions in amounts ranging from 0.001 to 5% by weight of a flavour composition, more preferably from 0.01 to 0.5% by weight. The compounds according to the present invention may be used for herbal flavour compositions, strawberry and raspberry compositions, brown flavour compositions, or tea compositions.

When used in fragrance applications, compounds of the present invention can be employed in wide ranging amounts depending upon the specific application and on the nature and quantity of other odourant ingredients, that may be for example, from about 0.001 to about 20 weight percent. In one embodiment compounds may be employed in a fabric softener comprising in amount of about 0.001 to 0.05 weight percent. In another embodiment compounds of the present invention may be in alcoholic solution in amounts of about 0.1 to 20 weight percent, more preferably between about 0.1 and 5 weight percent.

However, these values should not be limiting on the present invention, since the experienced perfumer and flavourist may also achieve effects or may create novel accords with lower or higher concentrations.

The compounds of the present invention may be employed into the fragrance application simply by directly mixing the fragrance composition with the fragrance application, or they may, in an earlier step be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application, comprising the incorporation of a compound of formula I as a fragrance ingredient, either by directly admixing the compound of formula I to the application or by admixing a fragrance composition comprising a compound of formula I, which may then be mixed to a fragrance application, using conventional techniques and methods.

As used herein, "fragrance application" means any product, such as fine perfumery, e.g. perfume and Eau de Toilette; household products, e.g. detergents for dishwasher, surface cleaner; laundry products, e.g. softener, bleach, detergent; body care products, e.g. shampoo, shower gel; and cosmetics, e.g. deodorant, vanishing creme, comprising an odourant. This list of products is given by way of illustration and is not to be regarded as being in any way limiting.

The compounds according to the present invention may be prepared according to a process wherein appropriately substituted cyclohexenones are reacted with allyl bromide or allyl chloride under reaction conditions well known to the person skilled in the art (Bull. Chem. Soc. Jpn., 2298-2303 (1993). The resulting alkylated cyclohexenones (formula II as shown below) may be converted in the presence of ethyl aluminium-dichloride or methyl aluminium-dichloride to provide compounds of formula I wherein $R^{12}$ and $R^{13}$ taken together represents an oxygen atom, as illustrated by compounds of formula Ia, Ib, and Ic in scheme 1. The conditions under which such Lewis acid catalyzed reactions may proceed is described for example by Snider et al. in the Journal of Am. Chem. Soc. 1980, 102, 5872-5880 which is herein incorporated by reference.

The resulting carbonyl group at C1 may be reduced and/or alkylated to give further compounds of formula I. Similarly, if there is a double bond at C6 and C8 this can be reduced in a known manner to give still further compounds of formula I.

tion may also be performed by photochemical induction. Surprisingly we found that compounds of formula Ia may be Scheme 1:

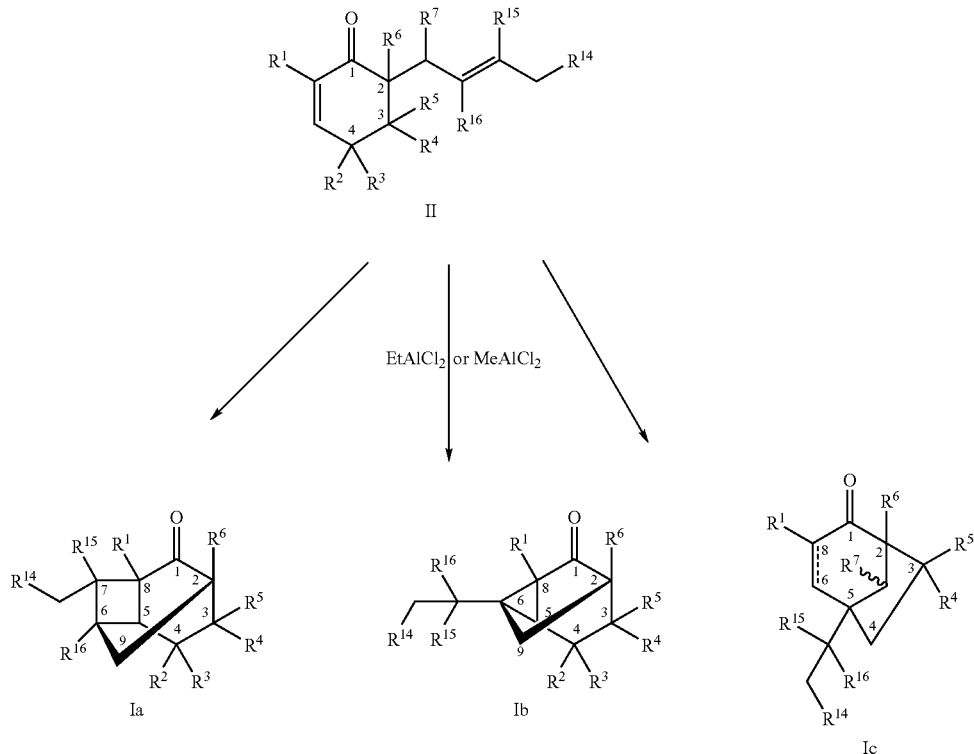

Compounds of formula II may also be prepared by alkylation of appropiately substituted phenols by reaction of the phenol with a metal hydride and an alkenylchloride (Greuter, H. et al. (1977) Helv. Chim. Acta, 60, 1701), followed by hydrogenation.

Whether a compound of formula Ia, Ib, Ic, or a mixture thereof is formed depends on the substituent pattern $R^2$, $R^3$, and $R^{16}$ of the alkylated cyclohexenone (II). A compound of formula Ic is formed as a main product if $R^2$, $R^3$, and $R^{16}$ of formula II are hydrogen. A mixture of compounds of formula Ia and Ib as main product is performed if $R^2$ and $R^3$ of formula II at the same time are not hydrogen. A mixture of compounds of formula Ia and Ic as main product is formed if $R^2$ and $R^3$ of formula II are hydrogen and $R^{16}$ of formula II is not hydrogen. The compounds are useful in flavour and/or fragrance compositions as mixtures, however, should one wish to use the compounds in pure form, they can be separated easily by purification processes, such as HPLC or preparative GC, according to the methodology known in the art.

The term "main product", as used herein with reference to single compounds, refers to a product comprising at least 50% by weight of that compound, more preferably more than 75% by weight, most preferably more than 90% by weight. When this term is used in relation to a mixture of compounds, e.g. one compound of formula Ia and one compound of formula Ic, it refers to a product comprising at least 50% by weight of this mixture, more particular more than 75% by weight, most particular more than 90% by weight.

The conversion of compounds of formula II for a selective preparation of compounds of formula Ia of the present invenformed by photochemically induced intramolecular [2+2] cycloaddition of compounds of formula I. For the photochemical induction a Hg-lamp may be used for a time period of about 1 to 15 hours. However, the induction time may depend on the solvent used and on additives such as sensitisers and Lewis acids. Preferred solvents are methanol, ethanol and iso propanol.

Thus, in another aspect the invention refers to a method of preparing compounds of formula Ia by photochemically induced cycloaddition.

Further particulars as to reaction conditions are provided in the examples.

There now follows a series of examples that illustrate the invention.

EXAMPLE 1 a) 2-Methyl-6-(3-methyl-but-2-enyl)-cyclohex-2-enone

To a solution of LDA (prepared from BuLi, 1.6 M in hexane, 75 ml, 0.12 mol and diisopropylamine, 12.2 g, 0.12 mol) in THF (50 ml) was added 2-methyl-cyclohex-2-enone (11.0 g, 0.1 mol) at −78° C. The mixture was stirred for 1 h at −78° C. and prenyl bromide 17.88 g, 0.12 mol) was added. The mixture was stirred over night, while the temperature was allowed to rise to room temperature. MTBE (50 ml) and sat. $NH_4Cl$ were added, the organic phase was separated and washed with brine, dried ($MgSO_4$) and concentrated in vacuo.

The residue was distilled in a Kugelrohr oven to yield 9.8 g (55%) of a slightly yellow oil.

$^1$H-NMR (400 MHz, CDCl$_3$): 6.82 (bs, 1H), 5.14-5.09 (m, 1H), 2.56-2.48 (m, 1H), 2.37-2.25 (m, 3H), 2.13-2.03 (m, 2H), 1.77 (s, 3H), 1.70 (s, 3H), 1.75-1.68 (m, 1H), 1.61 (s, 3H) ppm. $^{13}$C-NMR (100 MHz, CDCl$_3$): 201.6 (s), 144.3 (d), 135.1 (s), 133.0 (s), 121.8 (d), 46.9 (d), 27.8 (t), 27.7 (t), 25.7 (q), 25.0 (t), 17.6 (q), 16.0 (q) ppm. GC/MS (EI): 178 (M$^+$, 30), 168 (25), 123 (37), 110 (100), 95 (63), 83 (33), 69 (26), 53 (34), 41 (71), 39 (44). IR (ATR): 2966s, 2924s, 1672vs, 1451s, 1377s, 1181m, 1088m, 836m cm$^{-1}$.

b) 2.6-dimethyl-6-(3-methyl-but-2-enyl)-cyclohex-2-enone

Sodium hydride (60%, 85 g, 2.13 mol) was added portionwise to a solution of 2,6-dimethylphenol (250 g, 2.05 mol) in 2 L of toluene at 10-15° C. The resulting suspension was stirred for 45 min. The mixture was cooled to 5° C., and prenyl chloride (262 g, 2.13 mol, 85%) was added during 1.5 h keeping the temperature at 5° C. The mixture was then stirred for further 2 h at 10-15° C. Methanol (1 L) and palladium (2.5 g, 10% on charcoal) was added and the gray suspension was hydrogenated at 0.3 bar overpressure, keeping the temperature at 20-22° C. (ice bath). The suspension was then filtered through a pad of celite. The yellow filtrate was washed with water (0.5 L), aqueous sodium hydroxide (0.5 L) and brine (0.5 L), dried (MgSO$_4$) and concentrated in vacuo. The residue was distilled over a 5 cm Vigreux column to yield 318 g (81%, bp 78-82° C./0.05 Torr) of a colorless oil.

Odor description: fruity, grapefruit, minty, bergamot $^1$H-NMR (400 MHz, CDCl$_3$): 6.62 (bs, 1H, 3-H), 5.06-5.11 (m, 1H, 2'-H), 2.34-2.28 (m, 2H, 4-H), 2.25-2.14 (m, 2H, 1'H), 1.91 (dt, J$_{5a,5b}$=13.6 Hz, J$_{5a,4}$=6.1 HZ, 1H, 5$_a$-H), 1.76 (s, 3H, 2-CH$_3$), 1.77-1.70 (m, 1H, 5$_b$-H), 1.70 (s, 3H, 4'-H), 1.59 (s, 3H, 3'-CH$_3$), 1.05 (s, 3H, 6-CH$_3$) ppm. GC/MS (EI): 192 (M$^+$, 16), 124 (100), 109 (74), 82 (31), 69 (40), 41 (57). IR (ATR): 2965s, 2922s, 1667vs, 1449m, 1376m, 1033m cm$^{-1}$.

EXAMPLE 2

5-Isopropyl-1,3-dimethyl-bicyclo[3.2.1]oct-3-en-2-one

To a solution of 2,6-dimethyl-6-(3-methyl-but-2-enyl)-cyclohex-2-enone (5.00 g, 26.04 mmol) in toluene (40 ml) was added dropwise neat EtAlCl$_2$ (97%, 1.5 eq., 4.96 g, 39.06 mmol). During the addition, the temperature was kept below 10° C. The brown mixture was kept at room temperature over night and was then poured on icecold saturated NH$_4$Cl. The mixture was extracted with MTBE, washed with brine, dried (MgSO$_4$) and concentrated in vacuo. The residue was distilled bulb to bulb to yield 4.50 g (90%) of an colorless oil.

Odor description: woody, patchouli, vetiver, hesperidic $^1$H-NMR (400 MHz, CDCl$_3$): 6.86 (bs, 1H, 4-H), 1.81 (dt, J=11.0, 2.2 Hz, 1H, 8-H$_a$), 1.78-1.72 (m, 2H, 6-Ha, 7-H$_a$), 1.75 (d, J=1.6 Hz, 3-CH$_3$), 1.69 (sept, J=6.8 Hz, 1H, 5-CH(CH$_3$)$_2$), 1.64-1.53 (m, 2H, 6-Hb, 7-H$_b$), 1.37 (dd, J=11.0, 2.2 Hz, 1H, 8-H$_b$), 1.24 (s, 3H, 1-CH$_3$), 1.00 (d, J=6.8Hz, 3H, 5-CH(CH$_3$)CH$_3$), 0.93 (d, J=6.8 Hz, 3H, CH(CH$_3$)CH$_3$) ppm. $^{13}$C-NMR (100 MHz, CDCl$_3$): 205.2 (s, C-2), 151.7 (d, C-4), 133.1 (s, C-3), 52.4 (s, C-1), 51.8 (s, C-5), 50.7 (t, C-8), 34.8 (t, C-6), 34.8, (d, 5-CH(CH$_3$)$_2$), 33.3 (t, C-7), 20.7 (q, 1-CH$_3$), 19.0, 18.4 (2q, CH-(CH$_3$)$_2$), 15.6 (q, 3-CH$_3$) ppm. GC/MS (EI): 192 (M$^+$, 24), 177 (18), 149 (52), 136 (33), 121 (95), 110 (100), 91(46), 77 (39), 41 (41). IR (ATR): 2959s, 2867m, 1674vs, 1446m, 1362m, 1331m, 1030s cm$^{-1}$.

EXAMPLE 3

5-Isopropyl-1,3-dimethyl-bicyclo[3.2.1]octan-2-one

Prepared by hydrogenation of 5-isopropyl-1,3-dimethyl-bicyclo[3.2.1]oct-3-en-2-one. Mixture of 2 isomers (ratio of 5/1), main isomer: $^1$H-NMR (400 MHz, CDCl$_3$): 2.46-2.39 (m, 1H), 2.13-2.06 (m, 1H), 1.88-1.43 (m, 8H), 1.29-1.26 (m, 1H), 1.16 (s, 3H, 1-CH$_3$), 1.11 (d, J=7.2 Hz, 3H, 3-CH$_3$), 1.04-0.97 (m, 1H), 0.92 (d, J=6.8 Hz, 5-CH(CH$_3$)CH$_3$), 0.88 (d, J=6.8 Hz, 5-CH(CH$_3$)CH$_3$) ppm. $^{13}$C-NMR (100 MHz, CDCl$_3$): 219.6 (s, C-2), 52.7 (s), 46.3 (s) 44.7 (t), 38.7 (d), 37.9 (t), 37.5 (d), 36.3 (t), 36.4 (t), 20.4 (q), 18.4 (q), 17.4(q), 16.5(q) ppm. GC/MS (EI): 194 (M$^+$, 14), 151 (100), 133 (11), 123(48), 93 (29), 81 (83), 69 (19), 41 (30). IR (ATR): 2958s, 2868m, 1709vs, 1458s, 1369m, 999m cm$^{-1}$.

Odor description: woody, ambery, ionone

EXAMPLE 4-12

The following compounds were prepared according to the synthetic procedure of Example 2 from the correspondingly substituted materials and purified by chromatography where indicated.

Mixture of 5-tert-Butyl-1,3-dimethyl-bicyclo[3.2.1]oct-3-en-2-one and 1,5,7,8,8-Pentamethyl-tricyclo[3.3.1.0$^{2,7}$]nonan-6-one Prepared as a mixture and purified by chromatography.

a) 5-tert-Butyl-1,3-dimethyl-bicyclo[3.2.1]oct-3-en-2-one

Odor description: woody, patchouli, vetiver $^1$H-NMR (400 MHz, CDCl$_3$): 7.03 (bs, 1H, 4-H), 1.99 (ddd, J=16 Hz, 12 Hz, 5.6 Hz, 1H 8-H$_a$), 1.75 (d, J=1.6 Hz, 3-H, 3-CH$_3$), 1.75-1.53 (m, 5H), 1.47-1.40 (m, 1H), 1.25 (s, 3H, 1-CH$_3$), 0.98 (s, 9H, 5-C(CH$_3$)$_3$) ppm. $^{13}$C-NMR (100 MHz, CDCl$_3$): 204 (s, C-2), 152.6 (d, C-4), 132.3 (s, C-3), 54.2 (s), 51.9 (s), 46.9 (t, C-8), 33.5 (t), 32.9 (s, C(CH$_3$)$_3$), 30.7 (t), 25.9 (q, C(CH$_3$)$_3$), 20.7 (q, 1-CH$_3$), 15.5 (q, 3-CH$_3$) ppm. GC/MS (EI): 206 (M$^+$, 6), 191 (8), 149 (10), 135 (24), 124 (99), 110 (100) 91 (32), 77 (17), 57 (28), 41 (35). IR (ATR): 2961s, 2868m, 1673vs, 1467m, 1446m, 1365m, 1238m, 1030m, 879w cm$^{-1}$.

b) 1,5,7,8,8-Pentamethyl-tricyclo[3.3.1.0$^{2,7}$]nonan-6-one

Odor description: woody, patchouli $^1$H-NMR (400 MHz, CDCl$_3$): 2.19 (bs, 1H, 2-H), 1.78 (dd, J$_{9a,9b}$=12.8 Hz, J=2.0 Hz, 1H, 9-H$_a$), 1.76-1.50 (m, 4H, 3,4-H), 1.55 (d, J$_{9a,9b}$=12.8 Hz, 1H, 9-H$_b$), 1.05 (s, 3H, 8-(CH$_3$)$_a$), 0.98 (s, 3H, 5-CH$_3$), 0.97 (s, 3H, 7-CH$_3$), 0.96 (s, 3H, 1-CH$_3$), 0.63 (s, 3H, 8-(CH$_3$)$_b$) ppm. $^{13}$C-NMR (100 MHz, CDCl$_3$): 221.1 (s, C-6), 57.0 (s, C-7), 46.6 (d, C-2), 45.5 (s, C-8), 43.7 (s, C-5), 42.6 (t, C-9), 41.8 (s, C-1), 38.6 (t, C-4), 21.0 (q, 8-(CH$_3$)$_a$), 19.7 (2q, C-5, 8-(CH$_3$)$_b$), 18.1 (q, 1-CH$_3$), 10.8 (q, 7-CH$_3$) ppm. GC/MS (EI): 206 (M$^+$, 6) 191 (10), 124 (100), 109 (27), 97 (76), 69 (22)55 (17), 41 (31). IR (ATR): 2926m, 2862m, 1711s, 1446m, 1373m, 1004m, 761w cm$^{-1}$.

5-sec-Butyl-1,3-dimethyl-bicyclo[3.2.1]oct-3-en-2-one

Odor description: woody, vetiver, cedar, olibanum

Mixture of 2 isomers: $^1$H-NMR (400 MHz, CDCl$_3$): 6.86, 6.83 (2bs, 1H, 4-H), 1.95-1.51 (m, 7H), 1.75 (s, 3H, 3-CH$_3$), 1.40-1.32 (m, 2H), 1.23 (s, 3H, 1-CH$_3$), 1.00-0.90 (m, 6H) ppm. GC/MS (El): 206 (M$^+$, 8), 177 (17), 149 (41), 124 (100), 121 (82), 110 (98), 91 (42), 77 (32), 41 (43). IR (ATR): 2961s, 2865m, 1674vs, 1446s, 1364s, 1222m, 1034s cm$^{-1}$.

5-Isopropyl-3-methyl-bicyclo[3.2.1]oct-3-ene-2-one

Odor description: ambery, ciste, woody $^1$H-NMR (400 MHz, CDCl$_3$): 6.88 (bs, 1H, 4-H), 2.96 (dd, $J_{1,7a}$=7.4 Hz, $J_{1,8b}$=4.6 Hz 1H, 1-H), 2.15 (m, 1H, 7-H$_a$), 1.92 (bd, $J_{8a,8b}$=11.2 Hz, 1H, 8-H$_a$), 1.74 (d, J=1.2 Hz, 3H, 3-CH$_3$), 1.72 (sept, J=6.8 Hz, 1H, 5-CH(CH$_3$)$_2$), 1.72-1.58 (m, 2H, 6-H$_a$, 7-H$_b$), 1.52-1.45 (m, 1H, 6-H$_b$), 1.42 (ddd, $J_{8b,8a}$=11.2 Hz, $J_{8b,1}$=4.6 Hz, J=2.0 Hz, 8-H$_b$), 1.03 (d, J=6.8 Hz, 3H, 5-CH(CH$_3$)CH$_3$), 0.95 (d, J=6.8 Hz, 3H, 5-CH(CH$_3$)CH$_3$) ppm. $^{13}$C-NMR (100 MHz, CDCl$_3$): 204.1 (s, C-2), 152.1 (d, C-4), 133.2 (s, C-3), 51.2 (s, C-5), 50.2 (d, C-1), 43.3 (t, C-8), 34.6 (d, 5-CH(CH$_3$)$_2$), 33.8 (t, C-6), 25.5 (t, C-7), 19.0, 18.5 (2q, 5-CH(CH$_3$)$_2$), 15.2 (q, 3-CH$_3$) ppm. GC/MS (El): 178 (M$^+$, 49), 163 (61), 135 (50), 123 (21), 107 (100), 91 (59), 79 (46), 77 (39), 67 (23), 41 (47). IR (ATR): 2957s, 2871m, 1677vs, 1447m, 1358s, 1053m, 1018m, 918s cm$^{-1}$.

5,7-Diisopropyl-3-methyl-bicyclo[3.2.1]oct-3-en-2-one

Odor description: woody, elemi

Mixture of the endo/exo-isomers in a ratio of 2/1; main (endo) isomer: $^1$H-NMR (400 MHz, CDCl$_3$): 6.97 (bs, 1H, 4-H), 3.06 (dd, J=6.2, 4.4 Hz, 1H, 1-H), 2.03-1.96 (m, 2H), 1.87 (dd, J=12.8, 10.4 Hz, 1H), 1.76-1.51 (m, 3H), 1.72 (d, J=1.6 Hz, 3H, 3-CH$_3$), 1.39-1.33 (m, 1H), 1.00 (d, J=6.8 Hz, 3H), 0.96 (d, J=6.0 Hz, 3H), 0.91 (d, J=6.8 Hz, 3H), 0.85 (d, J=6.0 Hz, 3H) ppm. $^{13}$C-NMR (100 MHz, CDCl$_3$): 203.0 (s, C-2), 153.9 (d, C4), 134.0 (s, C-3), 54.4 (d, C-1), 50.2 (s, C-5), 48.5 (d, C-7), 44.4 (t, C-8), 39.1 (t, C-6), 34.7 (d), 32.4 (d), 22.2 (q), 21.7 (q), 18.6 (q), 18.3 (q), 15.0 (q, 3-CH$_3$) ppm. GC/MS (El): 220 (M$^+$, 17), 205 (8), 177 (22), 151 (28), 135 (32), 121 (30), 109 (100), 107 (50), 91 (47), 77 (29), 69 (35), 41 (52). IR (ATR): 2956s, 2872m, 1673vs, 1467m, 1365s, 973m, 903m cm$^{-1}$.

5-Isopropyl-3,7,7-trimethyl-bicyclo[3.2.1]oct-3-en-2-one

Prepared according to Example 2 with 2,5,5-Trimethyl-6-(3-methyl-but-2-enyl)-cyclohex-2-enone as starting material.

$^1$H-NMR (400 MHz, CDCl$_3$): 6.88 (bs, 1H, 4-H), 2.52 (d, $J_{1,8b}$=4.4 Hz, 1-H, 1-H), 1.98 (bd, $J_{8a,8b}$=11.2 Hz, 1H, 8-H$_a$), 1.80 (ddd, $J_{8b,8a}$=11.2 Hz, $J_{8b,1}$=4.4 Hz, J=2.0 Hz 1H, 8-H$_b$), 1.73 (s, 3H, 3-CH$_3$), 1.66 (sept., J=7.0 Hz, 1H, 5-CH(CH$_3$)$_2$), 1.53 (s, 2H, 6-H), 1.19 (s, 3H, 7-(CH$_3$)$_a$), 0.97 (d, J=7.0 Hz, 3H, 5-CH(CH$_3$)CH$_3$), 0.91 (d, J=7.0 Hz, 3H, 5-CH(CH$_3$)CH$_3$), 0.90 (s, 3H, 7-(CH$_3$)$_b$) ppm. $^{13}$C-NMR (100 MHz, CDCl$_3$): 203.7 (s, C-2), 152.2 (d, C-4), 133.3 (s, C-3), 62.4 (d, C-1), 51.7 (s, C-5), 48.5 (s, C-8), 42.6 (t, C -6), 38.8 (s, C-7), 35.0 (d, 5-CH(CH$_3$)$_2$), 32.2 (q, 7-(CH$_3$)$_a$), 27.5 (q, 7-(CH$_3$)$_b$), 18.5 (q), 18.2 (q) ppm. GC/MS (El): 206 (M$^+$, 35), 191 (26), 163 (25), 135 (100), 121 (50), 107 (98), 91 (73), 77 (53), 69 (29), 55 (34), 41 (81). IR (ATR): 2957s, 2870m, 1676vs, 1466m, 1359m, 1048w, 885w cm$^{-1}$.

Odor description: woody, resin

1,3,5-Trimethyl-1,5,6,7,8,8a-hexahydro-1,4a-ethano-naphthalen-2-one

Odor description: woody, patchouli, vetiver, cedar

Mixture of two isomers; $^1$H-NMR (400 MHz, CDCl$_3$, (1S*,4aR*,5S*,8aR*)-isomer, derived from HMQC): 6.63 (bs, 1H, 4-H), 1.77 (d, J=1.6 Hz, 3H, 3-CH$_3$), 1.78-1.68 (m, 3H, 8-H$_a$, 9-H$_a$, 10-H$_a$), 1.63-1.53 (m, 2H, $^9$-H$_b$, 10-H$_b$), 1.54-1.47 (m, 1H, 6-H$_a$), 1.50-1.44 (m, 1H, 7-H$_a$), 1.45-1.35 (m, 1H, 5-H), 1.42-1.36 (m, 1H, 8a-H), 1.22-1.14 (m, 1H, 8-H$_b$), 1.16 (s, 3H, 1-CH$_3$), 1.08-0.94 (m, 2H, 6-H$_b$, 7-Hb), 1.03 (d, J=6.8 Hz, 3H, 5-CH$_3$) ppm. $^{13}$C-NMR (100 MHz, CDCl$_3$): 205.0 (s, C-2), 147.2 (d, C-4), 134.7 (s, C-3) 61.3 (d, C-8a), 54.5 (s, C-1), 50.7 (s, C-4a), 41.2 (d, C-5), 34.8 (t, C-9), 33.2 (t, C-10), 31.8 (t, C-6), 25.9 (t, C-8), 21.8 (t, C-7), 18.8 (q, 1-CH$_3$), 16.6 (q, 5-CH$_3$), 15.6 (q, 3-CH$_3$) ppm. MS(mixture) (El): 218 (M$^+$, 96), 203 (12), 190 (7), 175 (13), 161 (7), 147 (17), 124 (100), 105 (20), 95 (58), 82 (22), 67 (8), 55 (13), 41 (24).

1,3,3,5,7,8,8-Heptamethyl-tricyclo[3.3.1.0$^{2,7}$]nonan-6-one

Prepared as a mixture and purified by chromathography.

Odor description: patchouli, vetiver, woody $^1$H-NMR (400 MHz, CDCl$_3$): 1.96 (bs, 1H, 2-H), 1.79 (dd, $J_{9a,9b}$=13.2 Hz, $J_{9a,4b}$=2.8 Hz, 1H, 9-H$_a$), 1.66 (d, $J_{9b,9a}$=13.2 Hz, 1H, 9-H$_b$), 1.59 (dd, $J_{4a,4b}$=13.2 Hz, J=1.0 Hz, 1H, 4-H$_a$), 1.48 (dd, $J_{4b,4a}$=13.2 Hz, $J_{4b,9a}$=2.8 Hz, 1H, 4-H$_b$), 1.08 (s, 3H, 5-CH$_3$), 1.04 (s, 3H, 8-(CH$_3$)$_a$), 1.04 (s, 3H, 7-CH$_3$), 1.03 (s, 3H, 3-(CH$_3$)$_a$), 0.97 (s, 3H, 1-CH$_3$), 0.83 (s, 3H, 3-(CH$_3$)$_b$), 0.58 (s, 3H, 8-(CH$_3$)$_b$) ppm. $^{13}$C-NMR (100 MHz, CDCl$_3$): 221.3 (s, C-6), 58.7 (d, C-2), 56.1 (s), 53.6 (t, C-4), 44.4(s), 44.3 (s), 41.6(s), 44.1 (t, C-9), 31.3 (s), 31.3 (2q, 3-(CH$_3$)$_{a,b}$), 21.2 (q, 8-(CH$_3$)$_a$), 20.3 (q, 5-CH$_3$), 19.8 (q, 1-CH$_3$), 18.9 (q, 8-(CH$_3$)$_b$), 13.4 (q, 7-CH$_3$) ppm. GC/MS (El): 234 (M$^+$, 28), 219 (20), 163 (15), 152 (43), 137 (62), 121 (49), 97 (199), 83 (18), 69 (25), 57 (72), 41 (69). IR (ATR): 2959m, 2919m, 2865m, 1712s, 1452m, 1374m, 1005m, 951m, 886 w cm$^{-1}$.

3,3,5,7,8,8-Hexamethyl-tricyclo[3.3.1.0$^{2,7}$]nonan-6-one

Prepared as a mixture and purified by chromatography.

Odor description: ambery, woody, pine resin, Grisalva $^1$H-NMR (400 MHz, CDCl$_3$): 2.32 (t, J=6.0 Hz, 1H, 1-H), 2.21 (d, J=6.0 Hz, 1H, 2-H), 1.90 (dd, J=13.2 Hz, 6.0 Hz, 1H, 9-H$_a$), 1.74 (dd, J=13.2 Hz, 2.6 Hz, 1H), 1.57 (d, J=13.2 Hz, 1-H), 1.48 (dd, J=13.2, 2.6 Hz, 1H), 1.17 (s, 3H), 1.04 (s, 3H), 1.00 (s, 3H), 0.97 (s, 3H), 0.84 (s, 3H), 0.64 (s, 3H) ppm. $^{13}$C-NMR (100 MHz, CDCl$_3$): 220.9 (s), 57.3 (s), 53.3 (t), 52.6 (d), 44.0 (s), 42.3 (s), 39.6 (d), 33.4 (t), 30.9 (s), 30.5 (q), 30.3 (q), 23.9 (q), 20.1 (q), 20.0 (q), 13.4 (q) ppm. GC/MS (El): 220 (M$^+$, 6), 205 (5), 164 (64), 152 (37), 137 (199), 123 (19), 91 (14), 69 (26), 55 (17), 41 (46). IR (ATR): 2956m, 2924m, 2866w, 1711s, 1451m, 1373m, 1012m, 956m, cm$^{-1}$.

Mixture of 3,3,5,8,8-Pentamethyl-tricyclo[3.3.1.0$^{2,7}$] nonan-6-one and 1-Isopropyl -3,3,5-trimethyl-tricyclo[3.2.1.0$^{2,7}$]octan-6-one Prepared as a mixture and purified by chromatography.

a) 3,3,5,8,8-Pentamethyl-tricyclo[3.3.1.0$^{2,7}$]nonan-6-one

Odor description: woody, patchouli, cedar, camphoraceous
$^1$H-NMR (400 MHz, CDCl$_3$): 2.61 (t, J=5.0 Hz, 1H, 7-H), 2.46 (bt, J=5.6 Hz, 1H, 2-H), 2.34 (bq, J=5.6 Hz, 1H, 1-H), 1.92 (dd, J$_{9a,9b}$=13.2 Hz, J$_{9a,1}$=5.6 Hz, 1H, 9-H$_a$), 1.73 (J$_{9b,9a}$=13.2 Hz, J=2.8 Hz, 1H, 9-H$_b$), 1.58 (d, J$_{4a,4b}$=13.6 Hz, 1H, 4-H$_a$), 1.49 (dd, J$_{4b,4a}$=13.6 Hz, J=2.8 Hz, 1H, 4-H$_b$), 1.32 (s, 3H, 8-(CH$_3$)$_a$), 1.02 (s, 3H, 3-(CH$_3$)$_a$), 0.97 (s, 3H, 5-CH$_3$), 0.82 (s, 3H, 3-(CH$_3$)$_b$), 0.75 (s, 3H, 8-(CH$_3$)$_b$) ppm. $^{13}$C-NMR (100 MHz, d$_6$-acetone): 219.0 (s, C-6), 57.6 (d, C-7), 53.2 (t, C-4), 47.2 (d, C-2), 44.3 (s, C-3), 40.7 (d, C-1), 40.6 (s, C-5), 33.6 (t, C-9), 29.9 (q, 3-(CH$_3$)$_a$), 29.8 (q, 3-(CH$_3$)$_b$), 29.8 (s, C-8), 27.1 (q, 8-(CH$_3$)$_a$), 21.6 (q, 8-(CH$_3$)$_b$), 19.8 (q, 5-CH$_3$) ppm. GC/MS (El): 206 (M$^+$, 17), 191, (15). 150 (29), 138 (145), 123 (64), 107 (48), 83 (100), 55 (29), 41 (48). IR (ATR): 2953m, 2866m, 1716vs, 1459m, 1373m, 1105m, 1002w, 931w, 898 w cm$^{-1}$.

b) 1-Isopropyl-3,3,5-trimethyl-tricyclo[3.2.1.0$^{2,7}$]octan-6-one

Odor description: woody, cedar, vertiver, fruity, patchouli
$^1$H-NMR (400 MHz, C$_6$D$_6$): 1.62 (d, J=8.3 Hz, 1H, 7-H), 1.59 (dd, J$_{8a,8b}$=11.2 Hz, J=2.4 Hz, 1H, 8-H$_a$), 1.52 (d, J$_{8b,8a}$=11.2 Hz, 8-H$_b$), 1.45 (dd, J$_{4a,4b}$=13.6 Hz, J=2.2 Hz, 1H, 4-H$_a$), 1.26 (d, J$_{4b,4a}$=13.6 Hz,1H, 4-H$_b$), 1.21-1.11 (m, 2H, 2-H, 1-CH(CH$_3$)$_2$), 1.01 (s, 3H, 5-CH$_3$), 0.99 (s, 3H, 3-(CH$_3$)$_a$), 0.96 (s, 3H, 3-(CH$_3$)$_b$), 0.83 (d, J=6.8 Hz, 3H, CH(CH$_3$)$_a$(CH$_3$)$_b$), 0.80 (d, J=6.8 Hz, 3H, CH(CH$_3$)$_a$(CH$_3$)$_b$) ppm. $^{13}$C-NMR (100 MHz, C$_6$D$_6$): 212.6 (s, C-6), 52.2 (t, C-4), 46.0 (d, C -2), 42.7 (s, C-5), 40.2 (s, C-1), 34.3 (t, C -8), 34.1 (d, C-7), 32.0 (2q, 3-(CH$_3$)$_{a,b}$), 31.9 (d, 1-CH(CH$_3$)$_2$, 29.2 (s, C-3), 18.9 (q, 5-CH$_3$), 18.8 (q, 1-CH(CH$_3$)$_a$(CH$_3$)$_b$), 18.7 (q, 1-CH(CH$_3$)$_a$(CH$_3$)$_b$)p pm. GC/MS (El): 206 (M$^+$, 41), 191 (37), 151 (15), 135 (36), 109 (100), 91 (38), 77 (24), 55 (21), 41 (43). IR (ATR): 2957m, 2926m, 2867m, 1725s, 1462m, 1317m, 1171m, 917m, 866m, 834m cm$^{-1}$.

EXAMPLE 13

5,7,8,8-Tetramethyl-tricyclo[3.3.1.0$^{2,7}$]nonan-6-one

A solution of 2,6-dimethyl-6-(3-methyl-but-2-enyl)-cyclohex-2-enone (10.0 g, 52.1 mmol) in methanol (250 ml) was irradiated using a Hg-lamp during 3 h. The solvent was evaporated in vacuo and the residue distilled in a Kugelrohr oven to yield 5.0 g of a colorless oil.

Odor description: patchouli, woody, camphoraceous
$^1$H-NMR (400 MHz, CDCl$_3$): 2.54 (m, 1H, 2-H), 2.23 (t, J=5.8 Hz, 1H, 1-H), 1.88 (dd, J$_{9a,9b}$=12.8 Hz, J=5.6 Hz, 1H, 9-H$_a$), 1.78 (d, J$_{9b,9a}$=12.8 Hz, 1H, 9-H$_b$), 1.88-1.52 (m, 4H, 3,4-H), 1.17 (s, 3H, 8-(CH$_3$)$_a$), 1.00 (s, 3H, 5-CH$_3$), 0.99 (s, 3H, 5-CH$_3$), 0.99 (s, 3H, 7-CH$_3$), 0.66 (s, 3H, 8-(CH$_3$)$_b$) ppm. $^{13}$C-NMR (100 MHz, C$_6$D$_6$): 217.6 (s, C-6), 58.1 (s, C-7), 42.7 (2s, C -5,8), 41.3 (d, C-1), 40.7 (d, C-2), 38.1 (t, C-4), 34.4 (t, C-9), 23.5 (q, 8-(CH$_3$)$_a$), 20.4 (q, 8-(CH$_3$)$_b$), 20.2 (q, 5-CH$_3$), 17.5 (t, C-3), 11.1 (s, 7-CH$_3$) ppm. GC/MS (El): 192 (M$^+$, 14), 177 (12), 149 (8), 124 (100), 109 (48), 93 (15), 82 (20), 69 (34), 53 (18), 41 (51). IR (ATR): 2923m, 2863m, 1710s, 1448m, 1375m, 1068m, 1020m, 1000m, 790w cm$^{-1}$.

EXAMPLE 14

5,6,7,8,8-Pentamethyl-tricyclo[3.3.1.0$^{2,7}$]nonan-6-ol

Prepared from 5,7,8,8-tetramethyl-tricyclo[3.3.1.0$^{2,7}$] nonan-6-one by reaction with methyl magnesium chloride.

Odor description: patchouli, woody, camphoraceous
$^1$H-NMR (400 MHz, C$_6$D$_6$): 2.23 (dd, J$_{9a,9b}$=13.2 Hz, J$_{9a,4a}$=3.2 Hz, 1H, 9-H$_a$), 2.12-2.09 (m, 1H, 2-H), 1.95 (dd, J$_{1,9b}$=6.8 Hz, J$_{1,2}$=6.0 Hz, 1H, 1-H), 1.62-1.49 (m, 3H, 4-H$_a$, 3-H$_{a,b}$), 1.43 (dd, J$_{9b,a}$=13.2 Hz, J$_{9b,1}$=6.8 Hz, 1H, 9-H$_b$), 1.37 (s, 3H, 8-(CH$_3$)$_a$), 1.26-1.18 (m, 1H, 4-H$_b$), 1.21 (s, 3H, 8-(CH$_3$)$_b$), 1.04 (s, 3H, 6-CH$_3$), 0.97 (s, 3H, 5-CH$_3$), 0.94 (s, 3H, 7-CH$_3$) ppm. $^{13}$C-NMR (100 MHz, C$_6$D$_6$): 79.6 (s, C-6), 50.4 (s, C-7), 42.1 (s, C-8), 41.7 (d, C-1), 38.7 (d, C-2), 36.9 (s, C-5), 36.5 (t, C-9), 35.8 (t, C-4), 27.9 (q, 8-(CH$_3$)$_a$), 24.9 (q, 6-CH$_3$), 21.6 (q, 8-(CH$_3$)$_b$), 20.9 (q, 5-CH$_3$), 18.0 (t, C-3) 12.8 (q, 7-CH$_3$) ppm. GC/MS (El): 208 (M$^+$, 1), 190 (22), 175 (28), 162 (9), 147 (48), 121 (73), 98 (59), 83 (37), 69 (19), 55 (31), 43 (100), 41 (43). IR (ATR): 3502br., 2947vs, 2902vs, 2902vs, 2869s, 1457s, 1371s, 1207m, 1110s, 1072s, 1045s, 922vs cm$^{-1}$.

EXAMPLE 15

A perfume for a shower gel with a woody-floral character

|  | parts per weight |
|---|---|
| Cedryl acetate | 5 |
| Citronellyl acetate | 2 |
| Linalyl acetate | 20 |
| Agrumex | 20 |
| Pheyl ethyl alcohol | 40 |
| Amyl cinnamyl aldehyde | 140 |
| Ambrettolide | 5 |
| Ambrofix | 4 |
| Bois Cedre ess. Virginie | 20 |
| Bois Gaiac ess. | 10 |
| Damascenone (10% in DPG) | 6 |
| Dipropylene glycol | 10 |
| Eucalyptus ess. | 24 |
| Galaxolide 50 BB | 381 |
| Hedione | 80 |
| Javanol | 2 |
| Lilial | 30 |
| Linalool synt. | 20 |
| Mandarine ess. | 30 |
| Moxalone | 40 |
| N 112 | 1 |
| Okoumal | 5 |
| Orange terpenes dist. | 60 |
| Rose abs. Turquie | 2 |
| Rose artess abs. | 10 |
| Rose oxide (10% in DPG) | 5 |
| Super muguet | 10 |
| Vanilline (10% in DPG) | 8 |
| 1,5,7,8,8-Pentamethyl-tricyclo[3.3.1.0$^{2,7}$]nonan-6-one | 10 |
|  | 1000 |

In this composition 1,5,7,8,8-Pentamethyl-tricyclo [3.3.1.0$^{2,7}$]nonan-6-one enhances and harmonizes the woody part. It underlines the patchouli aspect but gives also a new modern woody character. The compound blends well with the floral part of the perfume and provides volume without giving a heavy impression.

The invention claimed is:
1. A compound of formula I

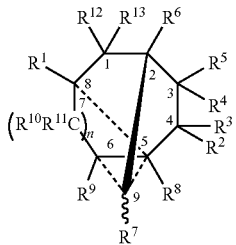

wherein
R$^1$, R$^4$, R$^6$ and R$^7$ are independently hydrogen, methyl or ethyl;
R$^2$ and R$^3$ are independently hydrogen, or C$_{1-5}$ alkyl; or
R$^2$ and R$^3$ together with the carbon atom to which they are attached form a 5- or 6-membered cycloylkyl ring;
R$^5$ is hydrogen, or C$_{1-4}$ alkyl;
R$^8$ is hydrogen, or branched lower C$_{3-7}$ alkyl;
R$^9$ is hydrogen, methyl, ethyl, or branched lower C$_{3-7}$ alkyl;
R$^{10}$ is ethyl or propyl;
R$^{11}$ is C$_{1-4}$ alkyl;
R$^{12}$ is hydroxy;
R$^{13}$ is hydrogen, or C$_{1-4}$ alkyl; or
R$^{12}$ and R$^{13}$ together with the carbon atom to which they are attached form a carbonyl group; the dashed line represents either a C—C single bond or no bond; and
a) when C5 and C8 are connected by a single bond and C9 and C6 are connected by a single bond, C9 and C5 are not connected by a bond,
n=1,
R$^7$, R$^8$ are hydrogen, and
R$^9$ is hydrogen, methyl or ethyl; or
b) when C5 and C8 are connected by a single bond and C9 and C6 are connected by a single bond, C9 and C5 are not connected,
n=0,
R$^7$, R$^8$ is hydrogen,
R$^9$ is a branched lower C$_{3-7}$ alkyl; or
c) when C5 and C8 are not connected by a bond, C9 and C5 are connected by a single bond,
R$^7$ is hydrogen, methyl or ethyl,
R$^8$ is a branched lower C$_{3-7}$ alkyl, or
R$^7$ and R$^8$ together with the carbon atoms to which they are attached form a 5- or 6-membered cycloalkyl ring,
n=0, and
the bond between C6 and C8 may be a single bond or a double bond.

2. A compound according to claim 1 having a formula Ia

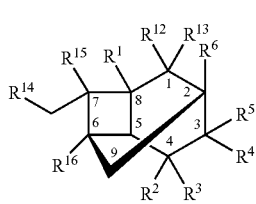

wherein
R$^1$, R$^4$, R$^6$, R$^{14}$ and R$^{16}$ are independently hydrogen, methyl or ethyl;
R$^2$ and R$^3$ are independently hydrogen, or C$_{1-5}$ alkyl; or,
R$^2$ and R$^3$ together with the carbon atom to which they are attached form a 5- or 6-membered cycloalkyl ring;
R$^5$ is hydrogen, or C$_{1-4}$ alkyl;
R$^{15}$ is C$_{1-4}$ alkyl;
R$^{12}$ is hydroxy;
R$^{13}$ is hydrogen or C$_{1-4}$ alkyl; or
R$^{12}$ and R$^{13}$ together with the carbon atom to which they are attached form a carbonyl group.

3. A compound according to claim 1 of formula Ib,

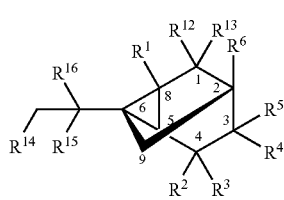

wherein
R$^1$, R$^4$, R$^6$, R$^{14}$ and R$^{16}$ are independently hydrogen, methyl or ethyl;
R$^2$ and R$^3$ are independently hydrogen, or C$_{1-5}$ alkyl; or,
R$^2$ and R$^3$ together with the carbon atom to which they are attached form a 5- or 6-membered cycloalkyl ring;
R$^5$ is hydrogen, or C$_{1-4}$ alkyl;
R$^{15}$ is C$_{1-4}$ alkyl;
R$^{12}$ is hydroxy;
R$^{13}$ is hydrogen or C$_{1-4}$ alkyl; or
R$^{12}$ and R$^{13}$ together with the carbon atom to which they are attached form a carbonyl group.

4. A compound according to claim 1 of formula Ic,

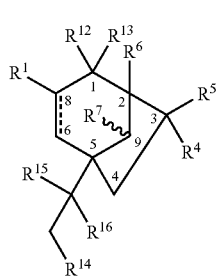

wherein
R$^1$, R$^4$, R$^6$, R$^{14}$ and R$^{16}$ are independently hydrogen, methyl or ethyl;
R$^5$ is hydrogen, or C$_{1-5}$ alkyl;
R$^7$ and R$^{14}$ are independently hydrogen, methyl or ethyl; or,
R$^7$ and R$^{14}$ together with the carbon atoms to which they are attached form a 5- or 6-membered cycloalkyl ring;
R$^{15}$ is C$_{1-4}$ alkyl;
R$^{12}$ is hydroxy;
R$^{13}$ is hydrogen or C$_{1-4}$ alkyl; or
R$^{12}$ and R$^{13}$ together with the carbon atom to which they are attached form a carbonyl group; and
the bond between C6 and C8 may be a single bond;
or the dotted line together with the bond between C6 and C8 may represent a double bond.

5. A compound according to claim 1 selected from the group consisting of 1,5,7,8,8-Pentamethyl-tricyclo [3.3.1.0$^{2,7}$]nonan-6-one; 1,5,7,8,8-Pentamethyl-tricyclo [3.3.1.0$^{2,7}$]nonan-6-one; 1,3,3,5,7,8,8-Heptamethyl-tricyclo [3.3.1.0$^{2,7}$]nonan-6-one; 3,3,5,7,8,8-Hexamethyl-tricyclo [3.3.1.0$^{2,7}$]nonan -6-one; 3,3,5,8,8-Pentamethyl-tricyclo [3.3.1.0$^{2,7}$]nonan-6-one; 5,7,8,8-Tetramethyl-tricyclo [3.3.1.0$^{2,7}$]nonan-6-one, 1-Isopropyl-3,3,5-trimethyl-tricyclo [3.2.1.0$^{2,7}$]octan-6-one; 5-Isopropyl-1,3-dimethyl-bicyclo[3.2.1]oct-3-en-2-one; 5-Isopropyl-1,3-dimethyl-bicyclo [3.2.1]octan-2-one; 5-tert-Butyl-1,3-dimethyl-bicyclo [3.2.1]oct-3-en-2-one; 5-sec-Butyl-1,3-dimethyl-bicyclo [3.2.1]oct -3-ene-2-one; 5-Isopropyl-3-methyl-bicyclo [3.2.1]oct-3-ene-2-one; 5,7-Diisopropyl -3-methyl-bicyclo [3.2.1]oct-3-en-2-one; 5-Isopropyl-3,7,7-trimethyl-bicyclo [3.2.1]oct-3-en-2-one; 1,3,5-Trimethyl-1,5,6,7,8,8a-hexahydro-1,4a-ethano-naphthalen -2-one; and 5,6,7,8,8-Pentamethyl-tricyclo[3.3.1.0$^{2,7}$]nonan-6-ol.

6. A flavour or fragrance composition comprising a compound according to claim 1.

7. A flavour or fragrance composition comprising at least one compound selected from the group of compounds of formula Ia

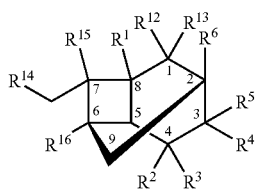

wherein
$R^1$, $R^4$, $R^6$, $R^{14}$ and $R^{16}$ are independently hydrogen, methyl or ethyl;
$R^2$ and $R^3$ are independently hydrogen, or $C_{1-5}$ alkyl; or,
$R^2$ and $R^3$ together with the carbon atom to which they are attached form a 5- or 6-membered cycloalkyl ring;
$R^5$ is hydrogen, or $C_{1-4}$ alkyl;
$R^{15}$ is $C_{1-4}$ alkyl;
$R^{12}$ is hydroxy;
$R^{13}$ is hydrogen or $C_{1-4}$ alkyl; or
$R^{12}$ and $R^{13}$ together with the carbon atom which they are attached from a carbonyl group
and at least one compound selected from the group of compounds of formula Ic as defined in claim 4.

8. A flavour or fragrance composition according to claim 7 comprising 5-tert-Butyl -1,3-dimethyl-bicyclo[3.2.1]oct-3-en-2-one and 1,5,7,8,8-Pentamethyl-tricyclo [3.3.1.0$^{2,7}$] nonan-6-one.

9. A fragrance application comprising the compound according to claim 1, wherein the fragrance application is a fragrance or a flavour application.

10. A fragrance application comprising the compound according to claim 1, wherein the fragrance application is selected from the group consisting of perfume, a household product, a laundry product, a body care product, and a cosmetic product.

11. The method of manufacturing a fragrance application or flavour application selected from: a perfume, a household product, a laundry product, a body care product or a cosmetic product which method comprises the step of: incorporating from 0.001 to 20% by weight of a compound according to claim 1 in said fragrance application or flavour application.

12. A method of manufacturing a flavour or fragrance composition, comprising the step of incorporating a compound of formula I as defined in claim 1 to a base material.

13. A method of manufacturing a fragranced application, comprising the incorporation of a compound of formula I as defined in claim 1.

14. A method according to claim 13 wherein the fragranced application is selected from the group consisting of perfume, household product, laundry product, body care product and cosmetics.

15. A process of preparing a compound of the formula I as defined in claim 1

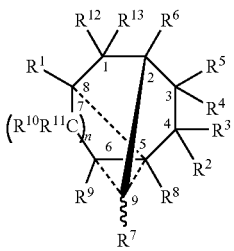

comprising the step of reacting a compound of formula II with ethyl aluminium dichloride or methyl aluminium dichloride

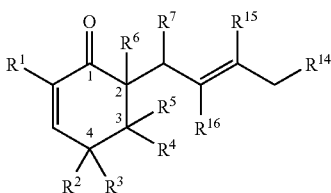

wherein
$R^1$, $R^4$, and $R^6$ are independently hydrogen, methyl or ethyl;
$R^2$ and $R^3$ are independently hydrogen, or $C_{1-5}$ alkyl; or
$R^2$ and $R^3$ together with the carbon atom to which they are attached form a 5- or 6-membered cycloylkyl ring;
$R^5$ is hydrogen, or $C_{1-4}$ alkyl;
$R^7$ and $R^{14}$ are independently hydrogen, methyl or ethyl; or
$R^7$ and $R^{14}$ together with the carbon atoms to which they are attached form a 5- or 6-membered cycloalkane ring;
$R^{16}$ is hydrogen, or lower branched $C_{3-7}$ alkyl,
and optionally followed by the step of reduction and/or alkylation of the carbonyl group at C1.

16. A process of preparing a compound of the general formula Ic

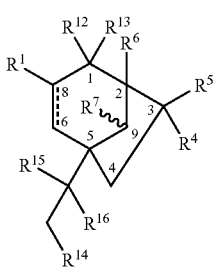

comprising the step of converting a compound of formula II by photochemical induction

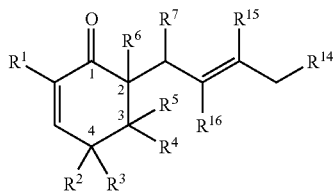

II wherein
R$^2$, R$^3$, and R$^{16}$ are hydrogen;
R$^1$, R$^4$ and R$^6$ are independently hydrogen, methyl or ethyl;
R$^7$ and R$^{14}$ are independently hydrogen, methyl or ethyl; or
R$^7$ and R$^{14}$ together with the carbon atoms to which they are attached form a 5- or 6-membered cycloalkane ring;
R$^5$ is hydrogen, linear or branched C$_{1-4}$ alkyl;
R$^{15}$ is linear or branched C$_{1-4}$ alkyl; and
and optionally followed by the step of hydrogenation across the double bond at C6 and C8, and
optionally followed by the step of reduction and/or alkylation of the carbonyl group at C1.

* * * * *